United States Patent
Kim et al.

(10) Patent No.: US 9,623,062 B2
(45) Date of Patent: Apr. 18, 2017

(54) ANTI-AGEING ACTIVITY OF CAMPHOR IN FIBROBLAST CELL LINE

(71) Applicants: Jeju National University Industryacademic Cooperation Foundation, Jeju-Si (KR); Urban Farmers Co., Ltd., Jeju-Si (KR)

(72) Inventors: Somi Kim, Jeju-Si (KR); Moonjae Cho, Jeju-Si (KR)

(73) Assignees: Jeju National University Industryacademic Cooperation Foundation, Jeju-Si (KR); Urban Farmers Co., Ltd., Jeju-Si (KR)

( * ) Notice: Subject to any disclaimer, the term of this patent is extended or adjusted under 35 U.S.C. 154(b) by 0 days.

(21) Appl. No.: 14/317,276

(22) Filed: Jun. 27, 2014

(65) Prior Publication Data

US 2015/0374771 A1 Dec. 31, 2015

(51) Int. Cl.
*A61K 36/28* (2006.01)
*A61K 31/125* (2006.01)

(52) U.S. Cl.
CPC ............ *A61K 36/28* (2013.01); *A61K 31/125* (2013.01); *A61K 2236/00* (2013.01)

(58) Field of Classification Search
None
See application file for complete search history.

(56) References Cited

U.S. PATENT DOCUMENTS

| | | | | |
|---|---|---|---|---|
| 4,603,146 A * | 7/1986 | Kligman | ............... | A61Q 19/08 514/559 |
| 5,153,230 A * | 10/1992 | Jaffery | ............... | A61K 8/362 514/23 |
| 5,435,997 A * | 7/1995 | Burns | ............... | A61K 8/38 424/401 |
| 6,352,690 B1 * | 3/2002 | Shabazz | ............... | A61K 8/31 424/401 |
| 2005/0158348 A1 * | 7/2005 | Schwarz | ............... | A61K 9/0014 424/400 |
| 2007/0031367 A1 * | 2/2007 | Brown | ............... | A61K 8/35 424/74 |

FOREIGN PATENT DOCUMENTS

WO   WO 2010088667 A1 *  8/2010   ............... A61K 8/34

OTHER PUBLICATIONS

Pillai et al. (2005) International Journal of Cosmetic Science, 27, 17-34.*
Website document entitled: "Chamomile (German) Hydrosol" (available at http://www.gardenofwisdom.com/catalog/item/3957554/3898448.htm). [archive to May 7, 2007]. Downloaded from website Sep. 16, 2016.*
Maier et al. "β-Galactosidase Activity as a Biomarker of Replicative Senescence During the Course of Human Fibroblast Cultures." *Ann. N.Y. Acad. Sci.* 1100(2007):323-332.
McKay et al. "Integrating Signals from RTKs to ERK/MAPK." *Oncogene.* 26(2007):3113-3121.
Ushio-Fukai et al. "Reactive Oxygen Species Mediate the Activation of Akt/Protein Kinase B by Angiotensin II in Vascular Smooth Muscle Cells." *J. Biol. Chem.* 274(1999):22699-22704.

* cited by examiner

*Primary Examiner* — Chris R Tate
*Assistant Examiner* — Russell Fiebig
(74) *Attorney, Agent, or Firm* — Mintz Levin Cohn Ferris Glovsky and Popeo, P.C.

(57) ABSTRACT

The present invention provides a composition for skin regeneration including chamomile hydrosol prepared by vacuum distillation as an active ingredient. The composition for skin regeneration including camphor or chamomile hydrosol prepared by vacuum distillation, which contains the camphor, exhibits to excellent skin regeneration ability to promote proliferation and migration of skin cells, and simultaneously include only components derived from natural herbal plants, and thus can be used in various forms such as medicine, quasi-drugs, cosmetics, and food materials without any of side effects.

2 Claims, 6 Drawing Sheets

ANTI-AGEING ACTIVITY OF CAMPHOR IN FIBROBLAST CELL LINE

BACKGROUND

The present invention relates to a composition for skin regeneration including chamomile hydrosol prepared by vacuum distillation as an active ingredient, and, more particularly, to a composition for skin regeneration including camphor ((1R)-1,7,7-Trimethylbicyclo[2.2.1]heptan-2-one) or chamomile hydrosol containing the camphor as an active ingredient, a cosmetic composition for skin regeneration and a food composition including camphor or chamomile hydrosol containing the camphor as an active ingredient, and a pharmaceutical composition for skin regeneration including camphor, pharmaceutically available salts thereof or chamomile hydrosol containing the camphor as an active ingredient.

Chamomile (*Matricaria recutita* L.) belongs to the family Compositae, and is widely used as herbal tea. From the old times, chamomile has been used to remove intestinal gases and relieve symptoms such as headache, insomnia, backache, neurodynia, rheumatism, skin diseases, dyspepsia, and gout. Among various kinds of chamomile, German chamomile has been widely used, and scientifically further evaluated. German chamomile contains bisabolol having low toxicity and sensitivity for the skin care. On the other hand, Roman chamomile, Anobillis and Moroccan chamomile do not contain bisabolol. In current studies, it was found that a chamomile essential oil has high antibacterial and antioxidant efficacies. The chamomile essential oil contains various phytochemicals including flavonoids, and some of the phytochemicals exhibit anti-inflammatory and anti-allergenic activities. The chamomile essential oil has been studied in various fields including pharmacy, perfume, cosmetics and food industries. However the activities of chamomile hydrosol have not been reported. In this study, therefore, we tried to demonstrate that chamomile hydrosol has a high effect in treating the skin like the essential oil.

Meanwhile, the key signaling pathways which regulate cell proliferation in various cells are PI3K and MEK/ERK pathways. The most distinguishing effect of PI3K is an increase in phosphorylated AKT. Activated AKT inhibits TSC1/TSC2 activities, and activates mTOR by phosphorylating Raptor. The activation of mTOR induces the S6K1 activities and phosphorylates 4E-BP1. Then, the phosphorylated 4E-BP1 is separated from eIF4E to become active, and enhances the cap-dependent translation of mRNA (Li-wei Rong, et al., RNA, 14(7): 1318-27, 2008). Another important pathway is the activation of a Ras/Raf/MEK/ERK cascade. Activated ERK can directly phosphorylate various transcription factors such as Ets, Elk, and Myc (M C Mendoza, et al., Mol Cell. 18; 41(6): 661-671, 2011).

An important indicator for proliferation of cells is an increase in reactive oxygen species (ROS). Generation of ROS appears not only in lesions but also in the cell proliferation in response to various kinds of stimuli. The vital role of ROS in normal physiological signaling is found in elevating transcription factors such as NF-κB, MAP kinases, and PI3K/AKT. It is known that ROS participate as a secondary messenger in the mitogenic signaling for cell proliferation, and increase tyrosine phosphorylations of tyrosine kinase receptors (TKRs), thus inducing the activation of downstream signaling cascades such as AKT, ERK, JNK, and like. Also, it is known that ROS could activate PI3K/AKT and ERK in culture cells such as fibroblasts, smooth muscle cells, and the like. However, ROS production is rather well known for causing damage to cells. Cells exposed to different concentrations of $H_2O_2$ can rapidly transform to harmful ROS, hence inducing the cell death (Masuko Ushio-Fukai, et al., The Journal of Biological Chemistry, 1996 (274), 22699-22704). The dual function of ROS was not well described yet, but different concentrations of ROS may show different effects on different targets within specific types of cells.

Fibroblasts are spindle-shaped cells, and are derived from multipotential mesenchymal cells, which are involved in the formation of fibers responsible for dermal architecture and elasticity. The fibroblasts play major roles in determining skin properties such as water retention and biomechanical properties by regulating extracellular matrix (ECM) components including collagens, elastin, and glycoproteins. The skin elasticity is influenced by the quality and quantity of elastin and collagen fibrils, which are degraded by an enzyme elastase. The increased enzymatic activities of elastase triggers various diseases, delays wound healing, and induces wrinkle formation. Also, the elastase plays an important role in controlling an inflammatory process. Therefore, developing elastase inhibitors is a novel anti-ageing strategy. Another biomarker for cellular senescence or ageing is the senescence-associated β-galactosidase activity, which is highly expressed and accumulated in lysosomes in senescent cells (Maier A B, et al., Ann NY Acad Sci. 2007 April; 1100: 323-32). β-Galactosidase catalyzes the hygrolysis into monosaccharides. The presence or absence of β-galactosidase activity is detected by X-gal, which produces a characteristic blue dye when cleaved by β-galactosidase.

Meanwhile, Korean Patent No. 1175803 discloses a 'cosmetic composition for skin cell regeneration and skin wrinkles attenuation,' and Korean Patent No. 0858629 discloses a 'cosmetic composition for increasing the skin energy comprising *Chamaecyparis obtusa*, *Pinus thunbergii* and *Pinus bungeana* extracts as active ingredients.' As disclosed in the present invention, however, the patent does not disclose a composition for skin regeneration comprising camphor or chamomile hydrosol prepared by vacuum distillation as an active ingredient. In the present invention, we tried to find that chamomile hydrosol extracted by vacuum distillation and camphor that is a main component of the chamomile hydrosol exhibit cell regeneration activities by activating the PI3K/AKT and ERK signaling pathways as the cells are treat with the chamomile hydrosol and camphor, and thus enhancing the cell viability.

Also, we tried to find that camphor enhances skin elasticity and protects dermal fibroblast from cellular senescence by attenuating the activities of elastase and β-galactosidase and enhancing a total expression level of collagens. Accordingly, in the present invention, we tried to confirm that the chamomile hydrosol extracted by vacuum distillation and camphor that is a main component of the chamomile hydrosol have anti-ageing activities, and are able to be used for a cosmetic composition for treating skin damage and improving the skin condition.

SUMMARY

An aspect of the present invention is to provide a composition for skin regeneration including camphor ((1R)-1,7,7-Trimethylbicyclo[2.2.1]heptan-2-one) or chamomile hydrosol containing the camphor as an active ingredient.

Another aspect of the present invention may provide a cosmetic or a food composition for skin regeneration and a food composition including camphor or chamomile hydrosol containing the camphor as an active ingredient.

Still another aspect of the present invention may provide a pharmaceutical composition for skin regeneration including camphor or a pharmaceutically available salt thereof, chamomile hydrosol containing the camphor as an active ingredient.

Yet another aspect of the present invention may provide use of the composition, and a therapeutic method using the composition.

The present inventors have found that chamomile hydrosol extracted by distilling chamomile under a vacuum induces cell proliferation and migration, and such effects are expressed by camphor that is a main ingredient of the chamomile hydrosol, developed compositions for skin regeneration exhibiting excellent skin regeneration ability and in vivo safety, which includes camphor or chamomile hydrosol prepared by vacuum distillation, which contains the camphor, as a main ingredient. Therefore, the present invention has been completed based on these facts.

Hereinafter, the present invention will be described in detail.

According to an aspect of the present invention, a composition for skin regeneration may include camphor ((1R)-1,7,7-Trimethylbicyclo[2.2.1]heptan-2-one) or chamomile hydrosol containing the camphor as an active ingredient.

The term "hydrosol" used herein refers to a liquid extract extracted by evaporating and condensing a chamomile raw sample using a method such as steam or vacuum distillation.

According to one exemplary embodiment of the present invention, the composition for skin regeneration including camphor or chamomile hydrosol containing the camphor as an active ingredient may induce proliferation and migration of cells. Here, the cells may be preferably fibroblasts, or epidermal keratinocytes (HaCat), but the present invention is not limited thereto.

According to one exemplary embodiment of the present invention, the camphor may be included at a content of 0.0005 to 0.004% by weight, based on the total weight of the composition, but the present invention is not limited thereto. When the content of the camphor is less than 0.0005% by weight, it is impossible to achieve an effect of the component to promote skin regeneration, whereas when the content of the camphor is greater than 0.004% by weight, it may be inefficient as an increase in the effect is not significant with respect to an increase in the content.

According to one exemplary embodiment of the present invention, the chamomile hydrosol may be prepared by distilling chamomile, preferably by distilling chamomile under a vacuum, more preferably extracting chamomile at a pressure of 95 to 100 kPa under a vacuum, and evaporating and condensing the chamomile, but the present invention is not limited thereto. The vacuum distillation is a conventional distillation method known in the related art. For example, any of distillation methods may be used without specified limitation as long as they can be performed so that the camphor in the chamomile hydrosol can be included at a content of 60% by weight or more, based on the total weight of the chamomile hydrosol.

According to one exemplary embodiment of the present invention, the chamomile hydrosol may be included at a content of 1.0 to 20% by weight, based on the total weight of the composition, but the present invention is not limited thereto. When the content of the chamomile hydrosol is less than 1.0% by weight, it is impossible to achieve an effect of the component to promote skin regeneration, whereas when the content of the chamomile hydrosol is greater than 20% by weight, it may be not efficient as an increase in the effect is not significant with respect to an increase in the content. Preferably, the chamomile hydrosol may include the camphor at a content of 60% by weight or more, preferably 60 to 90% by weight or more, based on the total weight of the chamomile hydrosol, but the present invention is not limited thereto.

According to another aspect of the present invention, a cosmetic composition for skin regeneration may include camphor or chamomile hydrosol containing the camphor as an active ingredient.

The cosmetic composition for skin regeneration according to one exemplary embodiment of the present invention may have a formulation selectable from the group consisting of a lotion, a toner, a face lotion, a nourishing cream, a massage cream, an essence, an eye cream, an eye essence, a cleansing cream, a cleansing foam, a cleansing water, a pack, a powder, a body lotion, a body cream, a body oil, and a body essence, but the present invention is not limited thereto.

In addition to the camphor or chamomile hydrosol containing the camphor according to one exemplary embodiment of the present invention, the cosmetic composition may also include adjuvants typically used in the field of cosmetics, such as fat components, organic solvents, dissolving agents, thickening and gelling agents, softening agents, antioxidants, suspending agents, stabilizing agents, foaming agents, aromatics, surfactants, water, ionic or nonionic emulsifying agents, fillers, sequestering and chelating agents, preservatives, vitamins, blocking agents, wetting agents, essential oils, dyes, pigments, hydrophilic or hydrophobic activating agents, lipid vesicles, or any other components typically used in the cosmetics.

According to still another aspect of the present invention, a pharmaceutical composition for skin regeneration may include camphor or a pharmaceutically available salt thereof, or chamomile hydrosol containing the camphor as an active ingredient.

In the pharmaceutical composition according to one exemplary embodiment of the present invention, the active ingredient, camphor, may be used per se, or may be used in the form of a pharmaceutically available salt in the field of pharmaceutics. The salt may be used without particular limitation as long as it is pharmaceutically available. For example, examples of the salt that may be used here may include hydrochloric acid, sulfuric acid, nitric acid, phosphoric acid, hydrofluoric acid, hydrobromic acid, formic acid, acetic acid, tartaric acid, lactic acid, citric acid, fumaric acid, maleic acid, succinic acid, methane sulfonic acid, benzene sulfonic acid, toluene sulfonic acid, naphthalene sulfonic acid, and the like. In addition to the acid addition salts, base addition salts such as sodium hydroxide, potassium hydroxide, triethylamine, tert-butylamine and the like may be used herein.

In the formulations of the pharmaceutical composition according to one exemplary embodiment of the present invention, the content of the active ingredient may vary according to the type of formulations, and may be determined according to ordinary methods.

The pharmaceutical composition according to one exemplary embodiment of the present invention may be optionally formulated by adding various adjuvants used in the field of medicine, for example, carriers, or other additives such as stabilizing agents, relaxing agents, emulsifying agents and the like as long as the adjuvants do not have a negative influence on the active ingredient.

Also, the composition according to one exemplary embodiment of the present invention may be administered parenterally, or orally. Routes of parenteral administration may be preferably routes of percutaneous administration. Among theses, routes of local application are most preferred. For example, the composition may be applied in the form of a plaster, but the present invention is not limited thereto. Any formulations suitable for pharmaceutical preparations, including ointments, creams, injections, powders, granules, tablets and the like, may be used as the formulation.

The pharmaceutical composition according to one exemplary embodiment of the present invention may be preferably administered at a dose of 0.001 to 1,000 mg/Kg·day, but the present invention is not limited thereto. Also, the composition according to one exemplary embodiment of the present invention may be administered alone or in combination of other drugs, or may be administered to assist the other drugs. In addition, for the composition of each formulation, the components other than the composition that is the above-described essential component may be optionally selected and blended by those skilled in the related art, depending on the kinds of formulations of other external applications, or a purpose of use. In this case, the components may exhibit a synergic effect when simultaneously used in combination of other materials.

According to still another aspect of the present invention, a food composition for skin regeneration may include camphor or chamomile hydrosol containing the camphor as an active ingredient.

When the composition according to one exemplary embodiment of the present invention may be used as a food additive, the composition may be added per se, or may be used in combination of other foods or food components. In this case, the composition may be used according to typical methods. The amount of the mixed active ingredient may be properly determined according to a purpose of use (prophylaxis, health, or therapeutic treatment). In general, in the preparation of foods or drinks, the composition according to one exemplary embodiment of the present invention may be added at a content of 15 parts by weight or less, preferably 10 parts by weight or less, based on the total amount of the raw materials. However, when the composition is administered for the purpose of health and hygiene or administered for an extended period of time for the purpose of health care, the dose of the composition may be less than or equal to this content range. However, since the active ingredient has no challenge in an aspect of safety, the active ingredient may be used even at a content exceeding this content range.

The kinds of the foods are not particularly limited. Examples of foods to which the materials may be added may include meats, sausages, breads, chocolates, candies, snacks, confectionery, pizzas, ramen, other noodles, gums, dairy products including ice creams, various soups, beverages, teas, drinks, alcoholic beverages, and vitamin combinations. In the typical meanings, the foods include all kinds of health foods.

Health drink composition according to one exemplary embodiment of the present invention may include a variety of flavoring agents or natural carbohydrates as additional components as in the conventional beverages. The above-listed natural carbohydrates that may be used herein may include monosaccharides such as glucose, and fructose, disaccharides such as maltose, and sucrose, and polysaccharides such as dextrine, and cyclodextrine, and sugar alcohols such as xylitol, sorbitol, erythritol, and the like. Natural sweetening agents such as thaumatin, and stevia extracts, or synthetic sweetening agents such as saccharine and aspartame may be used as the sweetening agents. The natural carbohydrates are generally added at a content of approximately 0.01 to 0.04 g, preferably approximately 0.02 to 0.03 g, based on 100 mL of the composition according to one exemplary embodiment of the present invention.

In addition to the above-described components, the composition according to one exemplary embodiment of the present invention may include various nutritional supplements, vitamins, electrolytes, flavoring agents, coloring agents, pectic acid and salts thereof, alginic acid and salts thereof, organic acids, protective colloidal thickeners, pH regulators, stabilizing agents, preservatives, glycerin, alcohol, carbonating agents used for carbonated drinks, and the like. In addition, the composition according to one exemplary embodiment of the present invention may include fruit pulps for preparing natural fruit juices, fruit juice drinks, and vegetable based beverages. Such a component may be used alone or in combination. The content of such additives is be of no importance, but may be generally selected in a range of 0.01 to 0.1 parts by weight, based on 100 parts by weight of the composition according to one exemplary embodiment of the present invention.

According to still another aspect of the present invention, the use of the composition may include applying the composition for skin regeneration, which includes camphor ((1R)-1,7,7-Trimethylbicyclo[2.2.1]heptan-2-one) or chamomile hydrosol containing the camphor as an active ingredient, to a target whose skin is to be regenerated.

The target whose skin is to be regenerated may include mammals, preferably humans.

According to one exemplary embodiment of the present invention, a method for improving skin condition comprising the step of applying the camphor ((1R)-1,7,7-Trimethylbicyclo[2.2.1]heptan-2-one) or chamomile hydrosol containing the camphor as an active ingredient to skin is provided. when the composition is applied to the target whose skin is to be regenerated, the composition has effects of attenuating skin AGEING, improving skin elasticity, preventing the skin AGEING, attenuating skin wrinkles, and treating skin damage.

According to yet another aspect of the present invention, a method of preventing and/or treating skin damage may include applying the composition for skin regeneration, which includes camphor ((1R)-1,7,7-Trimethylbicyclo [2.2.1]heptan-2-one) or chamomile hydrosol containing the camphor as an active ingredient, to the skin of a target in need of the composition.

BRIEF DESCRIPTION OF DRAWINGS

The above and other aspects, features and other advantages of the present invention will be more clearly understood from the following detailed description taken in conjunction with the accompanying drawings, in which:

FIGS. 3A-3B show the activities of fibroblasts using the chamomile hydrosol prepared by vacuum distillation and the results obtained by observing expression levels of proteins according to the treatment of camphor using western blot analysis according to an exemplary embodiment of the present invention: (FIG. 3A) Analysis of viabilities of fibroblasts when treated with the camphor at increasing concentrations of 0 to 260 µM; and (FIG. 3B) Determination of phosphorylation levels of PI3K, AKT, ERK, 4E-BP1, and mTOR using western blot analysis after the fibroblasts are treated with the camphor;

FIGS. 4A-4D show the experimental results for verifying that a low concentration of ROS formed by the treatment of camphor includes cell proliferation according to an exemplary embodiment of the present invention: (FIG. 4A) Comparison of levels of ROS formation on an hourly basis according to the treatment of camphor and hydrogen peroxide (control); (FIG. 4B) Removal of ROS according to treatment of NAC; (FIG. 4C) Measurement of cell viabilities according to treatment of NAC; and (FIG. 4D) Measurement of levels of phosphorylation using PI3K, AKT, ERK, 4EBP1 and β-actin-specific antibodies after the fibroblasts are treated with the camphor and NAC; and FIGS. 5A-5D show the results obtained by measuring the anti-ageing activities of the fibroblasts when treated with the camphor according to an exemplary embodiment of the present invention: (FIG. 5A) Images obtained by pre-treating fibroblasts with $H_2O_2$ (600 and 800 µM) for 72 hours and treating a fibroblast-free medium with camphor at a concentration of 260 µM for 48 hours, or synchronously treating the fibroblasts with camphor and $H_2O_2$ for 72 hours; (FIG. 5B) Diagram obtained by adding n-Suc-(Ala)-3-nitroanilide as a substrate and measuring levels of elastase activity inhibition while increasing concentrations of camphor gradually; (FIG. 5C) Measurement of total expression levels of collagen in cells treated with camphor to determine an inhibitory effect of camphor of elastases; and (FIG. 5D) Western blotting results of collagen types I, III and IV and collagenase MMP1.

DETAILED DESCRIPTION

Exemplary embodiments of the present invention will now be described in detail with reference to the accompanying drawings.

The disclosure may, however, be exemplified in many different forms and should not be construed as being limited to the specific embodiments set forth herein. Rather, these embodiments are provided so that this disclosure will be thorough and complete, and will fully convey the scope of the disclosure to those skilled in the art.

In the drawings, the shapes and dimensions of elements may be exaggerated for clarity, and the same reference numerals will be used throughout to designate the same or like elements.

Materials and Methods

1. Reagents

DMEM medium, bovine serum albumin (BSA), trypsin/EDTA, fetal bovine serum (FBS), Antibiotic-Antimycotic 100× were purchase from Invitrogen. 3-(4,5-dimethylthiazol-2-yl)-2,5-diphenyltetrazoliumbromide (MTT), 2'-7'-Dichlorodihydrofluorescein diacetate (DCFH-DA). Anti-PI3K, -AKT, -4E-BP1, -ERK, -β-actin antibodies were purchased from Cell Signaling (Danvers, Mass.), -MMP 1 was purchased from Cal Biochem, and -collagen I, III A1 from Santa Cruz. Polyvinylidene fluoride (PVDF) membranes for Western blotting were purchased from Bio-Rad (Hercules, Calif.). Amicon Ultra—2 mL 10K was purchased from Merck Millipore.

2. Sample and Hydrosol Preparation

A chamomile sample was prepared by collecting flower heads and leafy flowering stems of German chamomile (*Matricaria recutita* L.) in summer 2012. Here, the German chamomile were grown and produced in the farm Urban Farmers (Pyoseon-myeon, Seogwipo-si, Jeju-do, Korea), and the leafy flowering stems were approximately 30 cm long. A raw sample was extracted by steam distillation, or extracted from 95 kPa to 100 kPa fractions by vacuum distillation. In this case, the evaporated and condensed chamomile hydrosol was recovered, stored under refrigeration, and then used for experiments.

3. Cell Culture

Fresh human foreskin specimens were obtained from 8 donors aged from 6 to 12 years, who received a routine circumcision procedure of Jeju National University Hospital, Korea. After being digested with 0.1% dispose (Worthington Biochemical Corporation, Lakewood, N.J.) at 4° C. overnight, the epidermal layers were removed, and the remaining dermal parts were further digested with 0.1% collagenase I (Worthington) at 37° C. for another 4 h. The digested cells were then passed through a 70-mm cell strainer (BD Biosciences, Mississauga, ON, Canada), centrifuged, and resuspended in high-glucose DMEM (Gibco, Invitrogen, Carlsbad, Calif.), supplemented with 10% FBS (Gibco, Invitrogen, Carlsbad, Calif.), 100 U/ml penicillin, and 100 µg/ml streptomycin (all from PAA Laboratories, Linz, Austria). Cells were seeded on tissue culture plates at $1 \times 10^3$ cells/cm2, and maintained at 37° C. with 5% CO2. After 24 h, the plates were washed with PBS to remove residual non-adherent cells. The resulting adherent cells were grown to confluence within 7 days.

4. Measurement of Cell Viability

Primary dermal fibroblast ($2 \times 10^4$ cells/ml) cells were plated in 96-well plates in 200 µl of medium containing 10% FBS. After 24 h, the cells were treated with different concentrations of chamomile hydrosol or camphor. After treated, 20 µl of MTT solution (5 mg/ml) were added to each well and incubate in a humidified environment for 3-4 h. Adding 150 µl of DMSO after removed the supernatant in each well. Cell viability was determined from the absorbance at 570 nm, measured using a Sunrise microplate reader (Tecan, Salzburg, Austria). The blank contained 200 µl of DMEM with 10% FBS and equivalent reagent concentrations.

5. Flow Cytometric Analysis

To analyze the reactive oxygen species (ROS), the cells were seeded in 60 mm culture dishes at a density of $2 \times 10^4$ cells/mL, and then treated with 10% chamomile hydrosol for 0, 6, 12, and 24 hours. The cells were stained with 2'-7'-dichlorodihydrofluorescein diacetate (DCFH-DA) for 15 minutes, collected in a 15 mL tube, and then washed with PBS. The cells were re-suspended in 500 µl of PBS, and measured for a level of ROS. For the cell cycle analysis, the treated cells were harvested and fixed overnight in 70% ethanol at 4° C. After 24 hours, the cells were rehydrated in 2 mM EDTA-BPS with RNase A (25 ng/ml), and stained with PI (40 µg/ml). All the analyses were performed using a FACS Caliber flow cytometer (BD Biosciences), and each sample were analyzed by counting 10,000 cells.

6. Gas Chromatography-Mass Spectrometry (GC-MS)

Chromatographic analysis was carried out using a Shimadzu GC-MS (Model QP-2010, Shimadzu Co., Kyoto, Japan) in EI (Electron Impact) mode. The ionization voltage was 70 eV and temperatures of injector and detector were 250° C. and 280° C., respectively. The capillary column used was a Rtx-5MS (30 m length, 0.25 mm inner diameter, and 0.25 μm, film thickness). The oven temperature programmed at 80° C. was ramped to 200° C. at 5° C./min and to 280° C. at 5° C./min. Helium was used as the carrier gas at a flow rate of 1 ml/min, with an injector volume of 1 μl using 1:10 split ratio. The percentage of composition of the hydrosol was calculated by GC peak areas. GC-MS analysis of hydrosol was performed using Varian 3800 gas chromatography equipped with Varian 1200 l single quadruole Mass Spectrometer. The compounds were identified based on the comparison of their retention indices (RI), retention time (RT), mass spectra of WILEY, NIST library data of the GC-MS system and literature data (Adams, 2009)

7. Western Blot Analysis

After 0, 6, 12, 24 h treatment, cells were collected and lysed in lysis buffer (100 mM Tris-Hcl [pH 8], 250 mM NaCl, 0.5% Nonidet P-40, and 1× protease inhibitor cocktail) and sonicated few times then kept on ice for 30 min. The cell lysates were centrifuged at 13,000 rpm for 30 min at 4° C. The supernatant were collected and determined the concentration by BCA™ Protein assay (Pierce, Rockford, Ill.). For detecting MMP 1 and collagen I, and collagen III, we collected the media and centrifuging 400×g for 1 h at 4° C. by using Amicon Ultra 10K and determined the concentration by Bradford assay. Aliquots of the lysated were separated by 10-15% SDS-PAGE, and transferred to PVDF membranes using a glycine transfer buffer (192 mM glycine, 25 mM Tris-HCl [pH 8.8], and 20% [v/v] methanol). After blocking with Skim milk 5% overnight at 4° C., the membrane were incubated with primary antibodies for 1 h RT or overnight at 4° C. and then for 1 h with secondary antibodies. Primary antibodies were diluted at ratio 1:1000 whereas the anti-β-actin primary and secondary antibodies (horseradish peroxidase-conjugated goat anti-mouse IgG) (Vector Laboratories, Burlingame, Calif.) were diluted at ratio 1:10,000. Protein bands were detected using the WEST-ZOL® plus Western Blot Detection System (iNtRON, Gyeonggi-do, Korea).

8. Analysis of β-Galactosidase Activity

Fibroblast cells were incubated in 6-well plate at a density of 1×104 cells/well. Then the culture supernatants were removed and the cells were treated 72 h with only camphor (260 μM) or $H_2O_2$ 600 μM and 800 μM or co-treated camphor and $H_2O_2$ in fresh media; ethanol containing media and media only were used as negative controls. In some experiments, $H_2O_2$ was pretreated on fibroblast cells 72 h and replaced with or without camphor treatment (260 μM) 48 h. After treatment, cells were washed twice with PBS and fixed 10 minutes in 4% formaldehyde. Then, this was followed by washing 3 times with wash solution (100 mM $Na_2HPO_4$ set to pH 6 with 100 mM Citric Acid). Cells was incubated overnight at 37° C. in freshly made staining solution (5 mM $K_3Fe(CN)_6$, 5 mM $K_4Fe(CN)_6$, 2 mM $MgCl_2$, 150 mM NaCl, 40 mM $Na_2HPO_4$, 1 mg/mL bromochloro-indolyl-galactopyranoside (X-Gal), set to pH 6 with 100 mM citric acid). Next day, cells was washed the staining solution with PBS and taken picture by microscope and β-galactosidase-positive cell number ratio was calculated.

9. Elastase Assay

The inhibition of different concentrations of camphor on porcine pancreatic elastase (PPE (Type IV), Sigma) activity was examined using n-Suc-(Ala)3-nitroanilide as the substrate, and the release of nitroaniline was measured at 410 nm. The reaction was carried out in a 200 mM Tris-HCl buffer (pH 8.0) containing 0.8 mM N-Suc-(Ala)3-nitroanilide and 5 μg/mL elastase. Different concentrations of camphor (0-3200 μM) were added to the reaction mixture to reach a final volume of 320 μl, and elastase inhibition was assessed in 96 well-plate reader at 25° C. The reaction mixture was pre-incubated for 10 minutes before addition of the substrate. The change in absorbance was measured at 410 nm using a 96-well reader. The percentage of elastase activities was calculated by the following equation:

$$\text{Enzyme activity (\%)} = 100 - [(B-A)/A] \times 100]$$

wherein A represents an absorbance at 410 nm without camphor, and B represents an absorbance at 410 nm with camphor.

10. Total Collagen Assay

Total collagen was quantified in culture media using the Sircol Soluble Collagen Assay kit (Biocolor, Newtownabbey, Northern Ireland) by quantitative dye-binding method, according to the manufacturer's instruction. Fibroblast cells were seeded in 6-well culture plates at density $2 \times 10^5$ cells/well with 2 ml/well media with or without camphor (260 μM) and incubated for different time points (6 h, 12 h, 24 h). After treatment, 200 μl sample medium of each group was transferred to a 1.5 ml centrifuge tube and 1 ml Sircol dye reagent was added into each tube. The mixed contents were incubated at room temperature for 30 min. Then the tubes were centrifuged at 10000 g for 10 minutes. The supernatants were drained off and discarded. The remaining pellets were mixed with 1 ml Alkali reagent and gently mixed until the pellets dissolved completely. The solutions were transferred to a 96-well plate and read absorbance at 540 nm. A standard curve was made simultaneously by standard collagen stock solution (0.5 mg/ml).

Example 1

Effect of Camphor that is Main Ingredient of Chamomile Hydrosol on Cell Viability of Fibroblasts The skin is composed of various types of cells such as fibroblasts, corneous cells, and melanocytes. To assess the effect of chamomile hydrosol on the skin, fibroblasts were used.

Chamomile hydrosol was extracted using conventional methods such as steam distillation and vacuum distillation.

Figure 1:
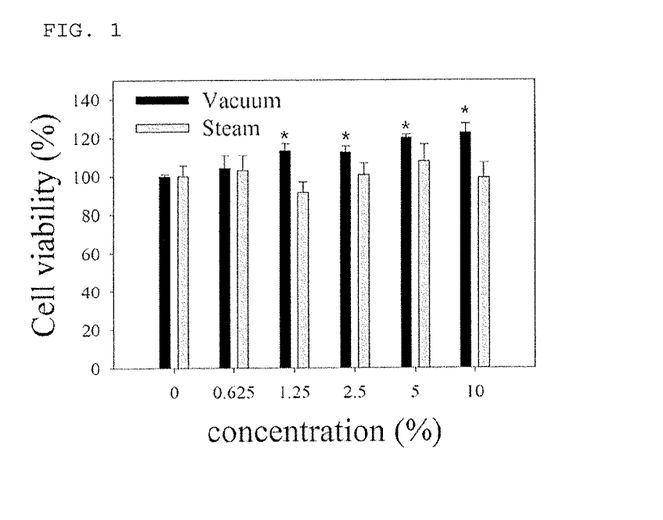
FIG. 1 shows the cell viabilities of fibroblasts after treatment of the fibroblasts with chamomile hydrosol prepared by vacuum or steam distillation according to an exemplary embodiment of the present invention.

As shown in FIG. 1, it was revealed that the chamomile hydrosol extracted by vacuum distillation showed an effect of over 20% cell proliferation in the fibroblasts. And, it could be seen that the chamomile hydrosol obtained by vacuum distillation increased the cell viability of the fibroblasts in a concentration-dependent manner, compared to the chamomile hydrosol obtained by steam distillation. By comparing the two processes: vacuum distillation and steam distillation by which the chamomile hydrosol was extracted, the chamomile hydrosol extracted by vacuum distillation induced the cell proliferation, but the chamomile hydrosol extracted by steam distillation did not induce the cell proliferation (FIG. 1), indicating that the different content of the main component has different influences on the chamomile hydrosol activities according to the extractions methods.

Figure 2A:
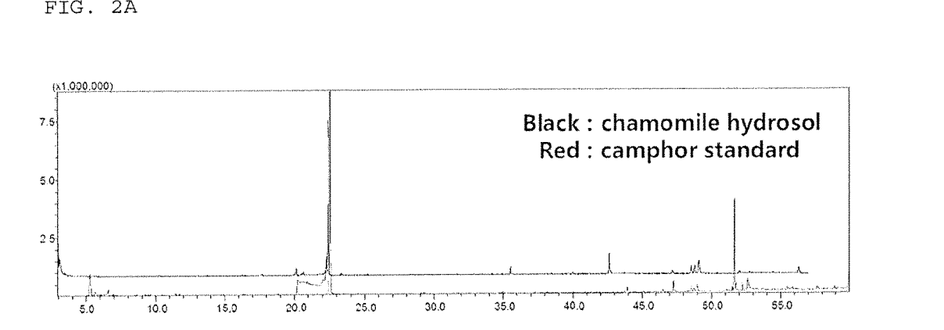
FIGS. 2A-2B show the analytical results obtained by comparing the peaks of camphor included in chamomile hydrosol prepared by vacuum distillation to the peaks of conventional camphor (Sigma) using GC/MS (FIG. 2A) and IR (FIG. 2B) according to an exemplary embodiment of the present invention.
Figure 2B:
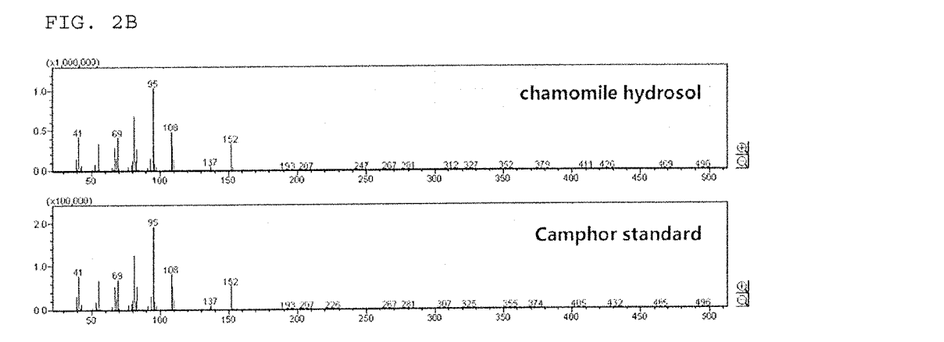

For this purpose, the components of the chamomile hydrosol extracted by vacuum distillation and the chamomile hydrosol extracted by steam distillation were analyzed using gas chromatography-mass spectrometry (GC-MS). The results of analyzing the components of the chamomile hydrosol using gas chromatography showed that the main component of the chamomile hydrosol extracted by vacuum distillation was camphor (FIGS. 2A and B). The GC-MS results showed that the chamomile hydrosol extracted by vacuum distillation included the camphor at a content of 68.11%, and the chamomile hydrosol extracted by steam distillation included the camphor at a content of 0.51% only (Table 1). When the camphor included in the camphor hydrosol was compared to the conventional camphor (Sigma), it was shown that the GC/MS and IR peaks were observed in the same positions (FIGS. 2A and 2B), indicating that the camphor as the main component played an important role in the cell viability.

TABLE 1

| No. | IR[a] | Name[b] | Area %[c] Vacuum | Area %[c] Steam |
|---|---|---|---|---|
| 1 | 716 | Dimethyl sulfoxide | 2.16 | 1.33 |
| 2 | 722 | Methyl 2-propane-1,1,1,3,3,3-D6-sulfonate | ND | 2.91 |
| 3 | 725 | 2,2,14,14-Tetramethyl-3,6,9,13-tetraoxa-2,14-disilapentadecane | ND | 2.44 |
| 4 | 728 | Propyl octyl ether | 0.28 | ND |
| 5 | 727 | Ethane, 1,1,2-trimethoxy- | ND | 8.33 |
| 6 | 728 | Ethylic acid | ND | 0.54 |
| 7 | 719 | n-octadecane | 4.84 | ND |
| 8 | 729 | Trimethylfluorosilane | ND | 0.53 |
| 9 | 1066 | 4-Pentenic acid, 4-Methyl-, Methyl ester | ND | 3.37 |
| 10 | 1098 | n-undecane | ND | 0.6 |
| 11 | 1147 | Camphor | 61.21 | 0.51 |
| 12 | 1156 | Dimethylsiloxanepentamer | ND | 0.5 |
| 13 | 1217 | 6-Phenyl-1,2-hexadiene | ND | 0.63 |
| 14 | 1515 | 2,4-Di-tert-butylphenol | 2.24 | 4.01 |
| 15 | 1610 | P-(2,2,3,3-tetramethylbutyl)phenol | ND | 0.53 |
| 16 | 1755 | Bisabolol oxide A | 8 | 5.65 |
| 17 | 1759 | Cyclobutane, 1,2-Diphenyl-, Trans | ND | 1.07 |
| 18 | 1088 | Bicyclo[2.2.1]heptan-2-one, 1,3,3-trimethyl-, (1R)- | 1.81 | ND |
| 19 | 1795 | Dicumene | ND | 0.7 |
| 20 | 1893 | Alpha-phenylacetophenone | ND | 0.52 |
| 21 | 1921 | Methyl palmitate | 1.31 | 19.35 |
| 22 | 1956 | Tridecylic acid | | 0.62 |
| 23 | 1661 | Alpha-Bisabololoxide-B | 0.51 | ND |
| 24 | 1967 | Butin-1, 4-Chloro-3-Methyl-3-Phenyl- | ND | 3.66 |
| 25 | 1974 | Quinolineethiodide | 3.26 | 3.36 |
| 26 | 2093 | Methyl linoleate | ND | 12.2 |
| 27 | 1964 | 5-Cyanotetralin | 3.1 | ND |
| 28 | 2098 | Methyl octadec-9-enoate | ND | 10.53 |
| 29 | 1099 | Linalool | 0.71 | ND |
| 30 | 2126 | Methyl stearate | ND | 0.89 |
| 31 | 2182 | Amide 16 | ND | 0.81 |
| 32 | 2238 | 4-Phenyl-1-pentene | 3.01 | 3.13 |
| | | Total | 92.5 | 88.72 |

[a]Retention indices relative to C7-C30 n-alkanes calculated on Rtx-5MS capillary column.
[b]Supercritical extract of chamomile hydrosol tentatively based on retention index and elution order as well as fragmentation pattern described in the literature
[c]Relative peak area percentage (peak area relative to the total peak area %)
ND: not detected Example 2

MAP Kinase and PI3K/AKT Pathways Activated Following Camphor Treatment

Figure 3A:
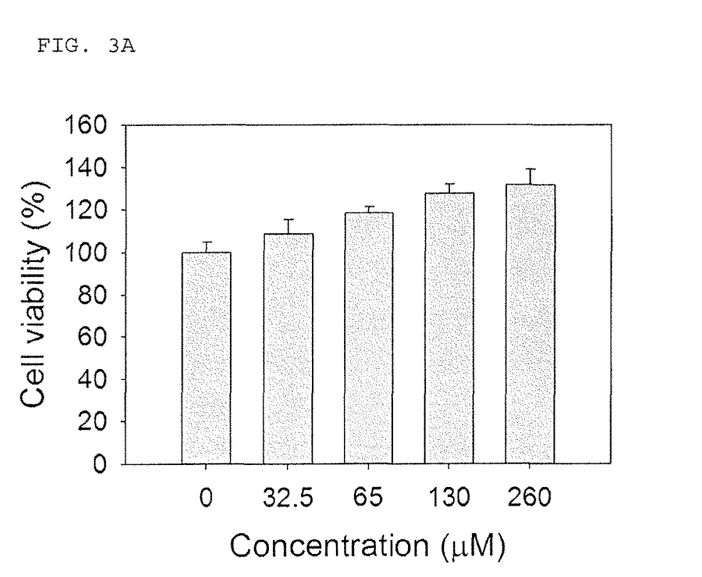
Figure 3B:
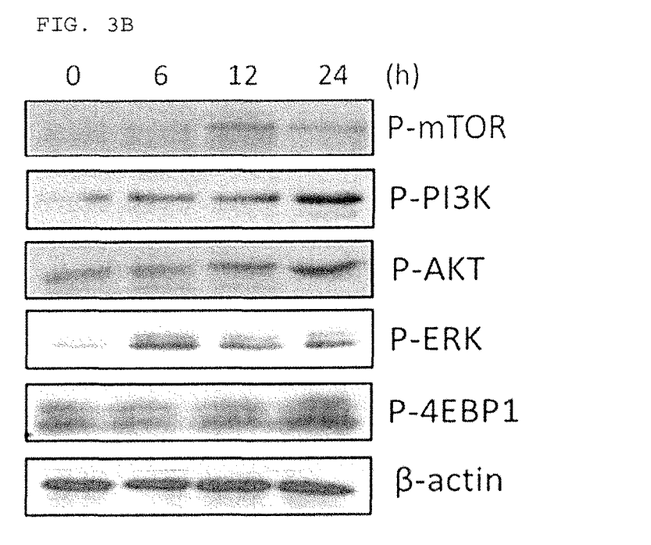

The camphor included in the chamomile hydrosol extracted by vacuum distillation was measured for fibroblast activity. The MTT results showed that the treatment of camphor increased the fibroblast viability from 32.25 µM to 260 µM (FIG. 3A). These data were consistent with the results showing that the chamomile hydrosol extracted by vacuum distillation had the fibroblast activity, but the chamomile hydrosol extracted by steam distillation, which did not include the camphor, had no fibroblast activity. Therefore, the present inventors concluded that the cell proliferation induced by the chamomile hydrosol extracted by vacuum distillation was due to the camphor. To understand that the fibroblast proliferation is due to the treatment of camphor, the present inventors investigated whether the camphor increased the cell viabilities through PI3K/AKT/mTOR, and MAP kinases. The fibroblasts were treated with the camphor in a time-dependent manner, and the expression levels of proteins were detected by western blot analysis. The results showed that the camphor increased the phosphorylation of PI3K, AKT, and ERK (FIG. 3B). The phosphorylated forms of 4E-BP1, which was known as an mRNA translation inhibitor, and an mTOR substrate were also observed (FIG. 3B). Based on these results, it could be seen that the camphor-induced fibroblast proliferation was triggered by up-regulating the PI3K/AKT and MAPK signaling cascades.

Example 3

Production of ROS by Treatment of Camphor

Figure 4A:
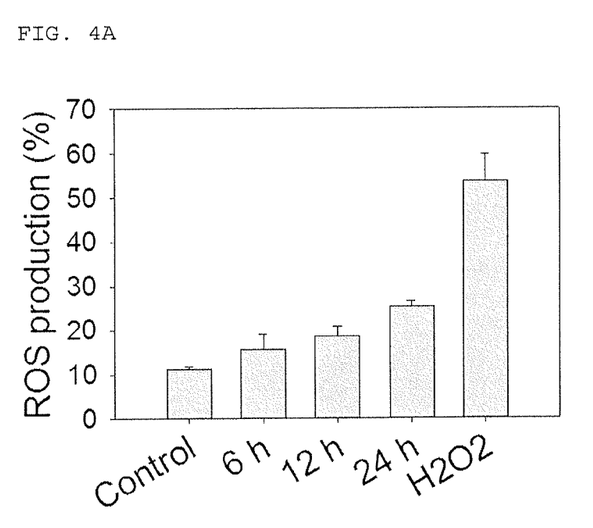

Production of ROS is known as a stress causing damage to DNAs or leading many cellular diseases. Also, it is involved in various kinds of cell death such as apoptosis, autophagy, and necrosis. However, ROS also plays an essential role in cell signaling and regulation. Since an increase in ROS levels is an indicator of cell proliferation, division and migration, production levels of ROS by the treatment of camphor in the fibroblasts were measured. $H_2O_2$ which was known to induce the cell death by elevating a toxic level of ROS was used as the positive control. Based on the measurement results, it was revealed that the camphor significantly increased the ROS production in the fibroblasts 24 hours after the treatment of camphor (FIG. 4A). The ROS production in the fibroblasts increased by approximately 13%, compare to the non-treated cell groups. On the other hand, the $H_2O_2$-induced ROS production increased by 53%. These production levels of ROS are consistent with the other reports showing that endogenous ROS could promote cell migration and proliferation at non-toxic levels. These results implied that signaling for cell viability was involved in ROS production, and the cell signaling was regulated by ROS in the fibroblasts. Based on the fact that the high-concentration ROS production induced cells toxicity but the low-concentration ROS production was able to induce the cell proliferation, it was proven that ROS produced by the treatment of camphor was able to induce the cell proliferation.

The fibroblasts were pre-treated with an ROS scavenger, N-acetyl-L-cysteine (NAC), and then treated with the camphor for 24 hours to examine the role of ROS in the cell proliferation.

Figure 4B:
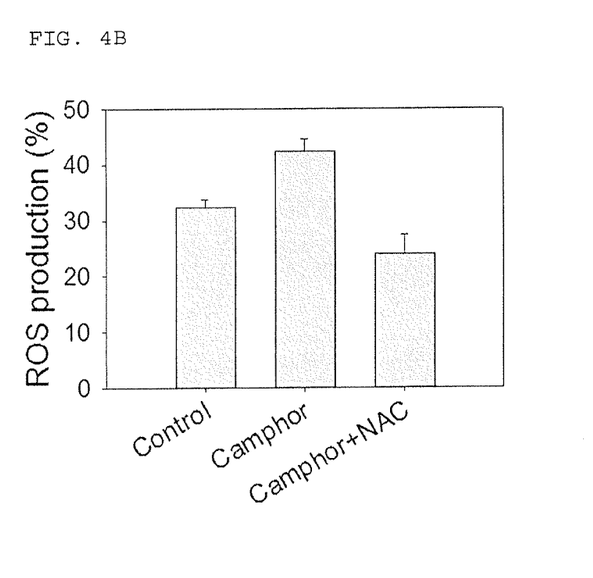
Figure 4C:
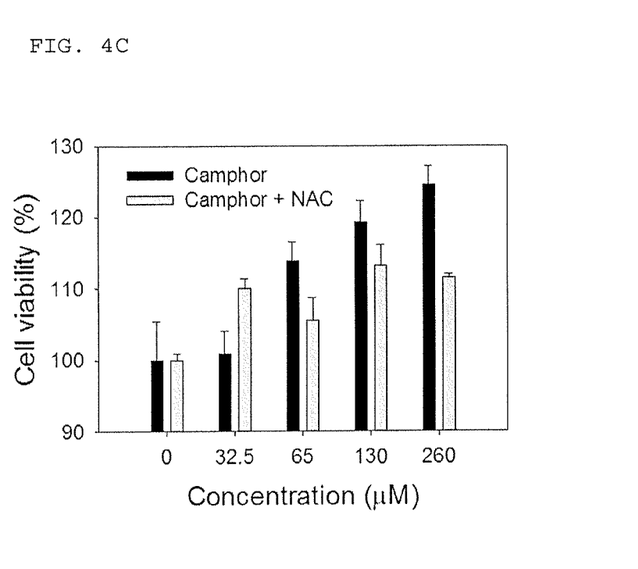

As a result, it was confirmed that the camphor decreased the induced ROS production, indicating the inhibitory effect of pre-treated NAC. Also, to examine an effect of the low-concentration ROS production on the cell proliferation, the cell viabilities by the treatment of NAC were measured (FIG. 4B). As a result, it was confirmed that the cell viabilities enhanced by the treatment of camphor decreased when ROS was scavenged by NAC (FIG. 4C).

Figure 4D:
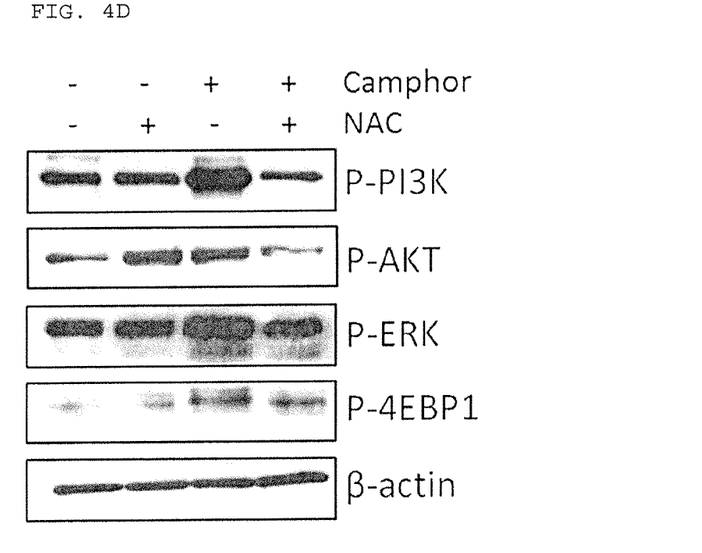

To confirm the effect of ROS in cell signaling, fibroblast cells were treated with NAC and camphor to detect protein expression level by western blot analysis. It is consistent with the above results that inhibition of ROS could down-regulate the active form of PI3K/AKT, and ERK. As shown in FIG. 4D, NAC pre-treatment reduced the phosphorylation of PI3K, AKT, 4EBP1, and ERK which was increased by the camphor. All together, we suggest that ROS play an important role in the proliferation of fibroblast cells.

Also, as ROS scavenged by the treatment of NAC, a change in expression of proteins associated with the cell proliferation was determined using western blot analysis. These analytical results were consistent with the results showing that inhibition of ROS could down-regulate the active forms of PI3K/AKT, and ERK. As shown in FIG. 4D, it could be seen that, when the expression of the proteins which were markers for cell proliferation were confirmed, the phosphorylation of PI3K, AKT, 4EBP1 and ERK which had been activated by the camphor decreased by scavenging ROS by the treatment of NAC (FIG. 4D). These results showed that the cell proliferation induced by the treatment of the camphor was dependent on ROS.

Example 4

Measurement of Anti-Ageing Activity of Camphor

Figure 5A:
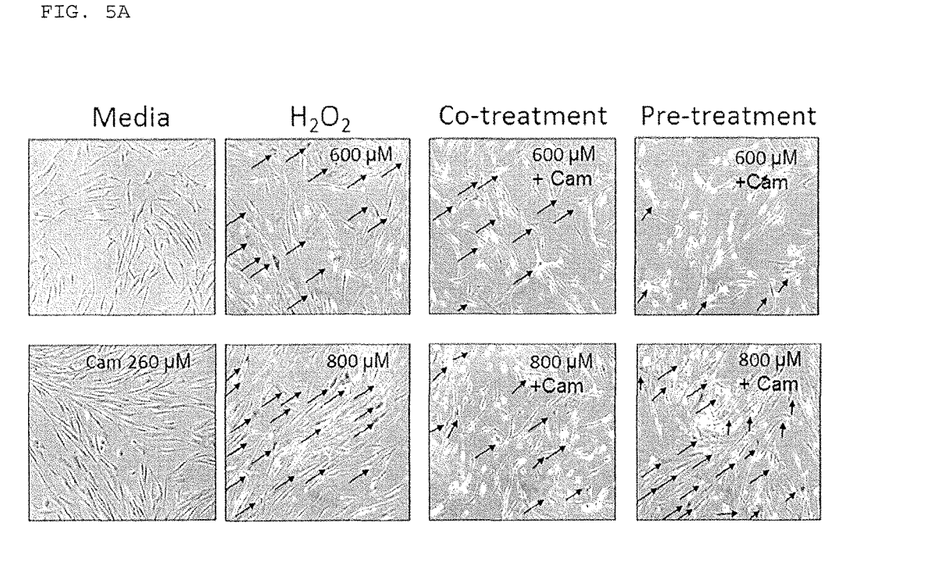

Fibroblasts are the most numerous cells within the dermal layer of skin, and thus play a critical role in preserving the structural integrity of the skin and healing the wounds. Since the proliferation of fibroblasts is induced by the treatment of camphor, the present inventors tested that the camphor had an effect to protect the skin cell ageing. One of the common biomarker for cellular senescence is an increase in senescence-associated β-galactosidase (SA-β-gal). As shown in FIG. 5A, induction of senescent cells by $H_2O_2$ dramatically induced SA-β-gal-positive cells, compared to the control. On the other hand, the co-treatment of the camphor with 600 and 800 μM $H_2O_2$ reduced the SA-β-gal-positive cells. Interestingly, it could be seen that the number of the senescent cells significantly decreased when the cells were pre-treated with 600 μM $H_2O_2$ for 3 days and then treated with the camphor for 2 days, implying that the camphor has an effect to recover the cellular senescence. However, it was revealed that the camphor did not significantly reverse the cellular senescence in the cells pre-treated with $H_2O_2$ at a concentration of 800 μM. This was due to the fact that the high toxicity of $H_2O_2$ made the senescent cells irrecoverable. These results indicated that the camphor induced the anti-ageing activities in the fibroblast cells.

Figure 5B:
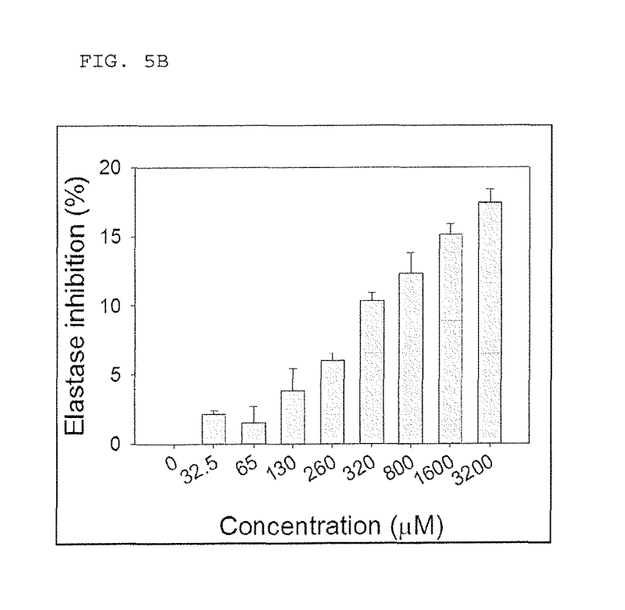

Also, the anti-ageing strongly correlates with the improvement of skin elasticity. For this reason, the skin elasticity was measured by the expression of elastin and collagen fibrils. That is, the effect of the camphor on the elastase activity that was a major cell marker during ageing or atherogenesis was examined. As a result, it was revealed that the camphor inhibited the elastase activity in a concentration-dependent manner, and had the highest inhibitory effect when treated at a concentration of 3.2M (FIG. 5B).

Figure 5C:
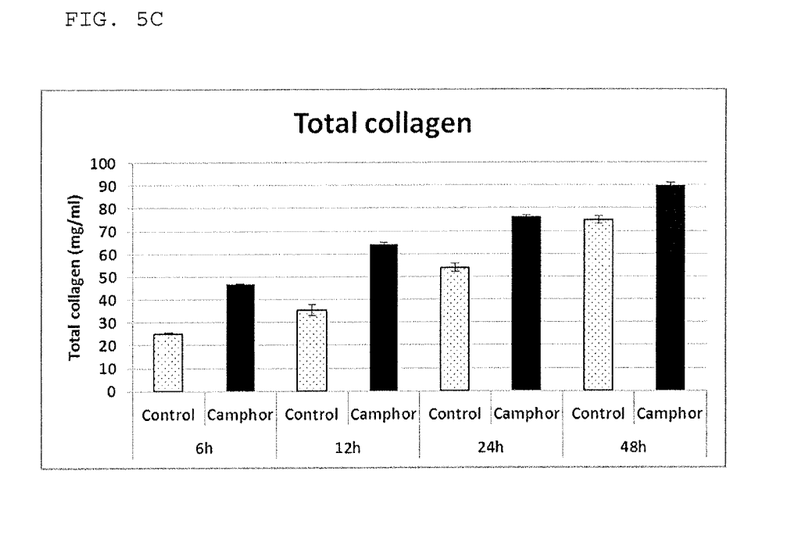
Figure 5D:
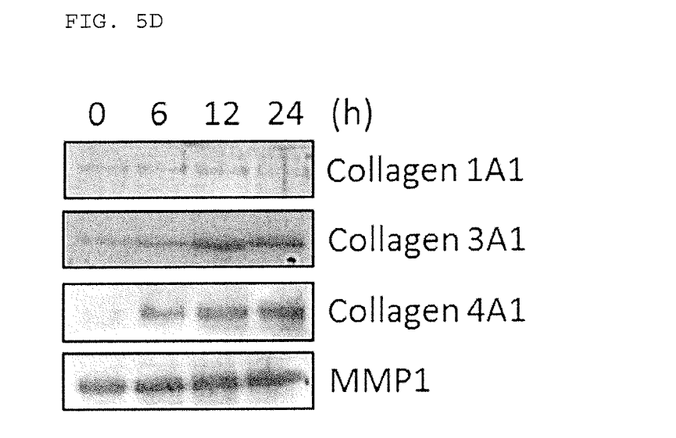

To confirm the inhibitory effect of the camphor on the elastases, the total expression level of collagen in the cells treated with the camphor were measured. As a result, it was shown that the total volume of collagen increased in the cells treated with the camphor, compare to the non-treated control (FIG. 5C). Also, the western blot results showed that the volume of collagen types III and IV increased by the treatment of camphor (FIG. 5D).

A known collagenase enzyme, MMP1, which can degrade collagen to cause damage to skin elasticity, was also examined. As a result, it was revealed that there was no change in the expression of MMP1, implying that the total volume of collagen induced by the camphor was altered by down-regulating the elastase rather than the collagenase.

From the results, it could be seen that the camphor had a high ability to protect the fibroblasts from AGEING by SA-β-gal inhibiting the elastase activity.

That is, it was concluded that the camphor had an anti-ageing activity, and thus was able to be used in the cosmetic compositions for treating skin damage and improving the skin condition.

Since the composition according to the exemplary embodiments of the present invention includes camphor, or chamomile hydrosol prepared by vacuum distillation, which contains the camphor, as a main ingredient, the composition exhibits to excellent skin regeneration ability to promote proliferation and migration of skin cells, and simultaneously include only components derived from natural herbal plants, and thus can be used in various forms such as medicine, quasi-drugs, cosmetics, and food materials without any of side effects.

While exemplary embodiments have been shown and described above, it will be apparent to those skilled in the art that modifications and variations can be made without departing from the spirit and scope of the present invention as defined by the appended claims.

What is claimed is:

1. A method for improving skin elasticity comprising topically applying to the skin of a subject in need thereof a composition comprising an effective amount of a camphor-containing chamomile hydrosol,
   wherein the chamomile hydrosol is prepared by distilling German chamomile (*Matricaria recutita* L.) under a vacuum, and
   wherein the camphor in the chamomile hydrosol is present at a content of at least 60% by weight of the chamomile hydrosol.

2. A method for attenuating skin wrinkles comprising topically applying to the skin of a subject in need thereof a composition comprising an effective amount of a camphor-containing chamomile hydrosol,
   wherein the chamomile hydrosol is prepared by distilling German chamomile (*Matricaria recutita* L.) under a vacuum, and
   wherein the camphor in the chamomile hydrosol is present at a content of at least 60% by weight of the chamomile hydrosol.

* * * * *

UNITED STATES PATENT AND TRADEMARK OFFICE
CERTIFICATE OF CORRECTION

PATENT NO. : 9,623,062 B2  
APPLICATION NO. : 14/317276  
DATED : April 18, 2017  
INVENTOR(S) : Somi Kim and Moonjae Cho

Page 1 of 1

It is certified that error appears in the above-identified patent and that said Letters Patent is hereby corrected as shown below:

On the Title Page

At Column 1, in the section designated "Assignees" (item (73)), please delete "Urban Farmers Co., Ltd., Jeju-Si (KR)".

Signed and Sealed this
Sixteenth Day of October, 2018

Andrei Iancu
*Director of the United States Patent and Trademark Office*